United States Patent [19]
Hassani et al.

[11] Patent Number: 5,983,701
[45] Date of Patent: Nov. 16, 1999

[54] NON-DESTRUCTIVE EVALUATION OF GEOLOGICAL MATERIAL STRUCTURES

[75] Inventors: Ferri P. Hassani, Beaconsfield; Afshin Sadri; Moe Momayez, both of Montreal, all of Canada

[73] Assignee: The Royal Institution for the Advancement of Learning, Montreal

[21] Appl. No.: 08/874,947

[22] Filed: Jun. 13, 1997

[51] Int. Cl.[6] .................................................. G01N 3/30
[52] U.S. Cl. ........................................... 73/12.01; 73/594
[58] Field of Search ................... 73/12.01, 12.09, 73/579, 594

[56] References Cited

U.S. PATENT DOCUMENTS

| | | |
|---|---|---|
| 3,097,523 | 7/1963 | Diamond et al. . |
| 3,224,253 | 12/1965 | McKay . |
| 3,504,532 | 4/1970 | Muenow et al. . |
| 3,641,811 | 2/1972 | Gnaedinger, Jr. et al. . |
| 3,732,725 | 5/1973 | Allen, Jr. et al. ............................ 73/81 |
| 3,854,328 | 12/1974 | Schmidt . |
| 4,163,393 | 8/1979 | Gutierrez et al. .......................... 73/584 |
| 4,542,639 | 9/1985 | Cawley et al. ........................... 73/82 X |
| 4,596,143 | 6/1986 | Norel ........................................ 73/598 |
| 4,702,111 | 10/1987 | Holland .................................... 73/579 |
| 4,702,112 | 10/1987 | Lawrie et al. ............................. 73/629 |
| 4,914,952 | 4/1990 | Miyajima et al. ......................... 73/598 |
| 4,918,988 | 4/1990 | Ebihara et al. ............................ 73/594 |
| 4,943,930 | 7/1990 | Radjy ....................................... 364/506 |
| 5,165,270 | 11/1992 | Sansalone et al. ..................... 73/594 X |
| 5,216,638 | 6/1993 | Wright ...................................... 367/35 |
| 5,325,702 | 7/1994 | Verstacten .......................... 73/12.09 X |
| 5,365,457 | 11/1994 | Madigosky .............................. 364/506 |
| 5,404,755 | 4/1995 | Olson et al. ............................... 73/639 |
| 5,426,972 | 6/1995 | Hertzler et al. ..................... 73/12.01 X |
| 5,490,411 | 2/1996 | Hogan ................................ 73/12.01 X |
| 5,540,096 | 7/1996 | Woodcock et al. ....................... 73/579 |
| 5,610,336 | 3/1997 | Svinkin .................................... 73/594 |
| 5,672,825 | 9/1997 | Uno et al. ................................. 73/579 |

OTHER PUBLICATIONS

Proceedings of the 2nd North American Rock Mechanics Symposium: NARMS 96, A Regional Conference of ISRM, Montreal Quebec, Canada,, Jun. 19–21, 1996, Rock Mechanics Tools and Techniques, Application of MSR for Evaluation of Excavated Tunnel and Shaft Concrete, F.P. Hassani, A. Sadri and M. Momayez pp. 875–882.

*Primary Examiner*—Thomas P. Noland
*Attorney, Agent, or Firm*—McFadden, Fincham

[57] ABSTRACT

A portable system for non-destructive evaluation of geological material structures comprises an impact device which impacts a spherical surfaced member against the surface of the structure. A vertical displacement transducer and a horizontal displacement transducer detect reflected signals from an interface of the structure, the signals being processed to give a indication of the depth of the interface from the surface of the interface and also provide an evaluation of the physical properties of the structure.

6 Claims, 3 Drawing Sheets

NON-DESTRUCTIVE EVALUATION OF GEOLOGICAL MATERIAL STRUCTURES

FIELD OF THE INVENTION

This invention relates to the non-destructive evaluation of geological material structures, and in particular relates to a portable apparatus for evaluation of such structures in confined environments, and to the method of carrying out such evaluation.

BACKGROUND OF THE INVENTION

By geological material is meant artificial or natural materials, such as concrete or rock.

The assessment of the condition of concrete shaft and tunnel linings in underground excavations is difficult since most of the deterioration processes take place in the rock-side or blind-side (in the rock/concrete interface of the lining). Ground water and variations in stress conditions are the main causes and can result in deterioration and damage to the linings. The traditional method of evaluating linings is to extract core samples from the structure and measure the thickness, locate delaminations and test for strength and elastic properties. However, coring is costly and can cause further damage. It would therefore, be advantageous to be able to use non-destructive methods of evaluation.

While seismic systems are known for evaluating underground rock formations by reflective elastic waves, such systems, with their associated apparatus, are quite large, and are not usable in confined spaces.

SUMMARY OF THE INVENTION

The present invention provides a compact miniature seismic reflection system (hereinafter referred to as MSR) which is portable and capable of being used in confined spaces. It is non-destructive and provides for evaluation of the conditions of a concrete or similar structure. The condition of a back-side of a structure, positions of any faults and inclusions in the structure, and the strength and elastic properties of the structure are readily determined.

In accordance with one aspect of the invention's portable apparatus for a non-destructive evaluation of geological material structures comprises an impactor having a spherical impact surface for positioning against a surface of the structure, a vertical displacement transducer and a horizontal displacement transducer for positioning on the surface of the structure adjacent the impactor, and processing means for processing signals from the transducers to indicate measurements from the surface of the structure to an interface and to indicate the physical properties of the structure. The impactor can be adapted for manual holding against the surface.

In accordance with another aspect of the invention a method of non-destructive evaluation of concrete and similar structures comprises impacting a spherical surface on the surface of the structure, detecting reflected signals by a vertical displacement transducer, detecting reflected signals by a horizontal transducer, processing signals from the transducers to produce a measurement between the surface and an interface in-the structure and a measurement of the physical properties of the structure.

The method provides for the evaluation of deterioration of subsurface structures, in particular deterioration occurring at an interface between the structure and the surrounding soil or rock.

BRIEF DESCRIPTION OF THE DRAWINGS

The invention will be readily understood by the following description, in conjunction with the accompanying diagrammatic drawings, in which.

DESCRIPTION OF PREFERRED EMBODIMENTS

Figure 1:
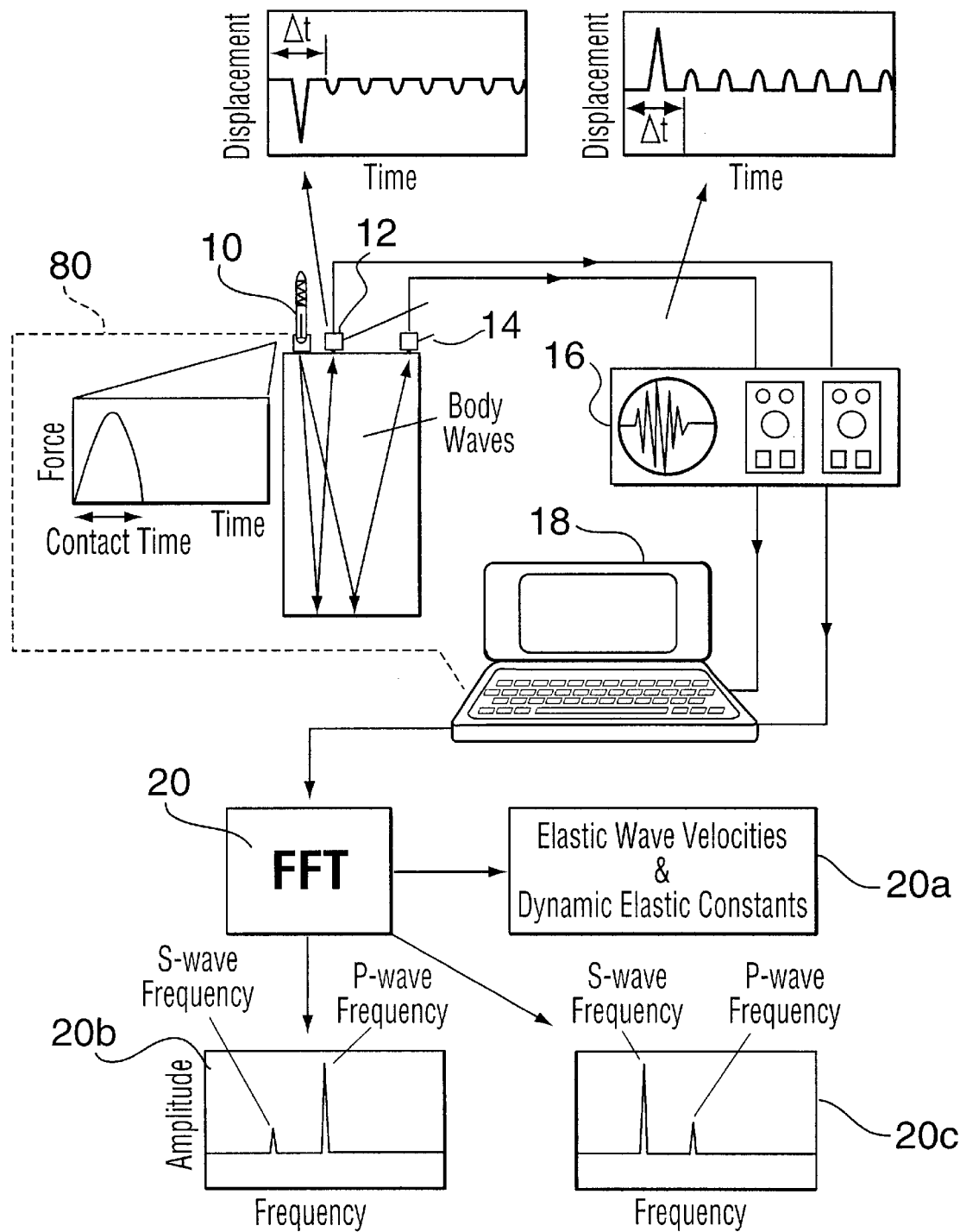
FIG. 1 is a schematic illustration of the whole apparatus.

The MSR system functions based on the impact-echo principle. FIG. 1 shows a schematic representation of the MSR system. In general the MSR non-destructive testing system involves an impact source 10, two broad band displacement transducers 12,14, an analog to digital signal converter card (A/D card) or a digital oscilloscope 16 and a portable computer 18. Also illustrated in FIG. 1 diagrammatically, is a Fast Fourier Transform (FFT) program 20, which converts the signals from time domain to frequency domain. The FFT program 20 is actually part of the programming within the computer 18 and results in outputs comprising elastic wave velocities and dynamic elastic constants 20a and the S & P wave waveforms 20b and 20c as shown. In practice these outputs, deriving from the FFT and other programming in this computer can be viewed on the computer monitor, and can also be recorded.

Similarly, the physical oscilloscope 16 can be embodied in the computer 18.

The impact body is released to cause an impact on the surface of the media. The impact of the spherical tip of the impact body results in generation of stress signal into the medium. The stress signal transforms into the body waves and surface waves, depending on the material quality of the medium. The body waves travel into the test object and any change in the acoustic properties of the medium results in their reflection toward the source direction. The change of acoustic properties could be as a result of any internal cracks or flaws or different material such as rocks. The reflected wavefronts are picked up by the transducers. The vertical displacement transducer is sensitive to the vibrations caused by the P-wavefronts at a right angle to the surface. The tangential displacement transducer is sensitive to the vibrations caused by the S-wavefronts parallel to the surface. The signals are amplified and transferred to an A/D card. The sampling rate and number of data points were arranged as required, for each test on the A/D card. Although measuring the time between arrivals of the P- and S-waves at the surface is complicated, the measurements can be converted into a frequency domain spectrum. The time domain waveforms are transferred to a portable computer to be converted into frequency domain spectra by the fast Fourier transform (FFT) technique. The frequency spectra is generated by a signal processing software and displayed by the portable computer for the required analysis. The frequency associated with the stress wave resonance between the two surfaces (e.g. top surface/flaw or top/bottom surfaces) becomes readily identifiable.

Figure 2:
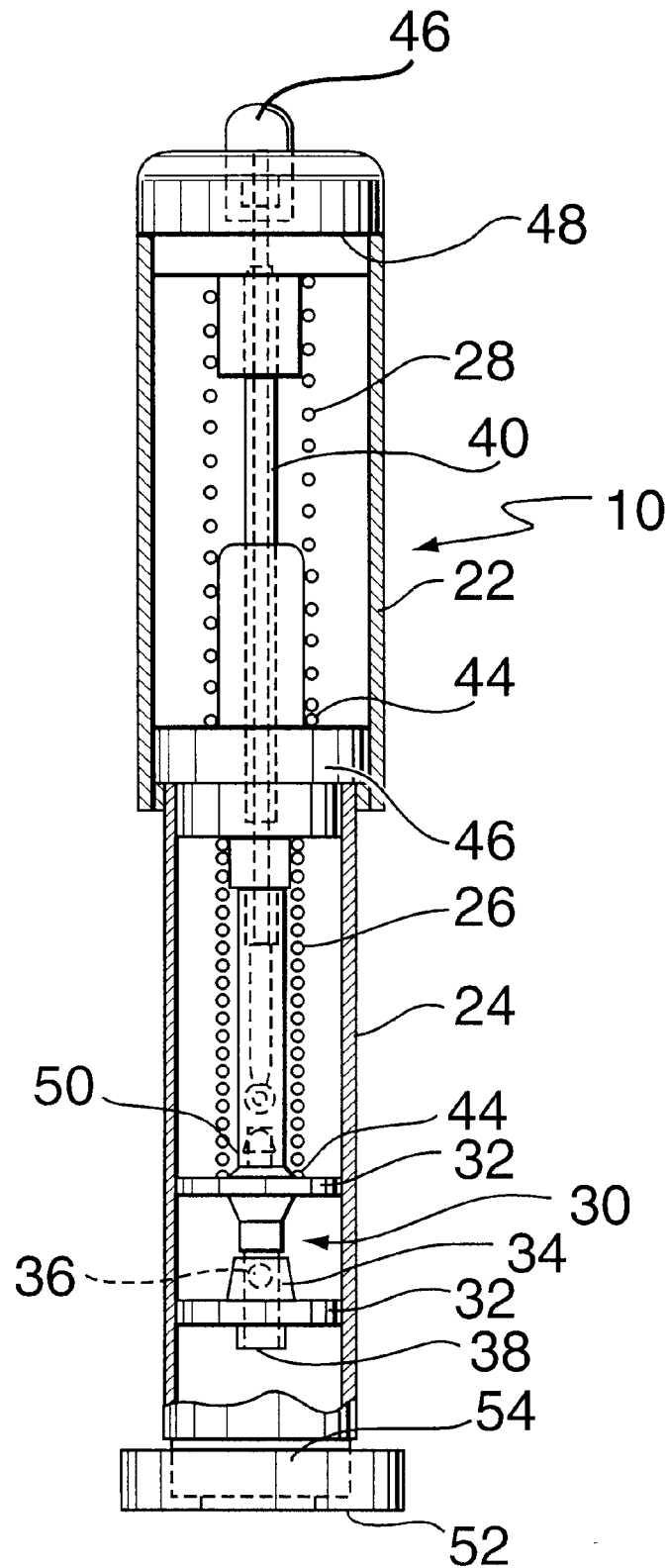
FIG. 2 is a longitudinal cross-section through a form of impact device.

An impact source, or device, is illustrated in more detail in FIG. 2. The device comprises a body 10 having a loading tube 22 and a guide tube 24, an impact spring 26 and a loading spring 28. Slidable axially in the guide tube 24 is a plunger unit 30 having spaced guides 32 connected by a tube 34 and within the tube 34 is a ball 36. The ball is held in the inner end of the tube, for example by a magnet (not shown) and the tube is open at the outer end 38.

An actuating rod 40 extends axially through the body. The loading tube 22 contains the loading spring 26 which acts at its lower end 44 on the closed end 46 of the guide tube 24. The loading tube 22 is slidable on the outside of the guide tube 24. The outer end 46 of the actuating rod 40 extends through the outer end 48 of the loading tube 22. The lower or inner end 50 of the actuating rod releasably engages with the plunger unit 30.

In FIG. 1 the impact device is shown in a "loaded" condition. In use, the impact device is held against the surface of a structure to be tested, the lower or inner end 52 against the surface. The plunger unit 30 is under a loading by the spring 26. The plunger unit is released by pushing on the end 46 of the rod 40. The plunger unit is forced towards the end 52 by the spring 26 but is stopped by engaging with a stop member 54 at the end of the tube 24 just before the inner end 38 would touch the structure surface. This causes the ball 36 to be impelled along the tube 34 to impact on the structure surface. The ball rebounds off of the surface.

The impact device is reloaded by pushing down the loading tube 22 over the guide tube 24. This causes the lower or inner end of the rod 50 to reengage with the plunger unit. The ball 26 is also again retained by the magnet. By releasing the loading tube 22 it is pushed outward by the loading spring 28, which retracts the plunger unit against the impact spring 26.

The size of the impact tip will vary in accordance with the impact strain required. Typical tip diameters and mass and energy constants are as follows:

SPECIFICATIONS OF MSR IMPACT DEVICES

| Hammer Diameter | Mass of Impact Body (g) | Impact Energy (Nmm) | Impact Strain Concrete (mm/mm) $\mu$/g |
|---|---|---|---|
| 1.3 | 11.1 | 27.0 | $0.77 \times 10^{-5}$ |
| 1.5 | 10.8 | 24.0 | $2.32 \times 10^{-5}$ |
| 3.0 | 5.4 | 11.0 | $2.75 \times 10^{-5}$ |
| 15.0 | 19.2 | 42.0 | $3.86 \times 10^{-5}$ |

A typical impact device has a 16.5 cm length and 3.0 cm diameter. The four impact devices are capable of producing impacts having time durations (contact times) between 16 to 40 $\mu$s on the smooth concrete and rock surfaces. The small diameters are used for thin slabs or thicknesses or short length specimens and the larger diameters are applied where the rock or concrete body are thick and longer wave lengths are required.

Impact of the impact bodies on the surface of a solid involves very short loading times with transient pulses of only few tis in duration. The short duration, low energy transient impacts are responsible for generating low strains in the range of $10^{-5}$ high rates of loading which causes strain rates in the range of $10^{+5}$ $\mu\epsilon$/s and low stresses in the medium. The range of strain properties generated by the impact devices are to classify MSR system as an apparatus capable of measuring dynamic elastic properties. Knowing that the static methods are identified by their slow rate of loading, strains in the range of $10^{-2}$, strain rates in the range of $10^{-3}$ $\mu\epsilon$/s and high stresses in the medium.

The transient impact of a spherical object on surface of a solid generates P- and S-(body) waves as well as R-(surface) wave. A spherical impact source acts as a point source which is responsible for generating spherical body waves in a solid. The duration of the impact or contact time, $t_c$, is an important parameter in MSR testing. The contact time is mainly controlled by the diameter of the sphere and surface conditions of the testing surface. The smaller the diameter of the sphere and the smoother the surface of the testing area is, the shorter the contact time of impact will become. The contact time controls the frequency content of the waves generated by the impact. The force-time function of the impact can be approximated as a half-cycle sine curve. The width of the curve is the contact time. The time-history of R-wave produces a vertical surface displacement. The time-history of the R-wave has the shape of the force-time function of the impact. Therefore, the force-time function of the R-wave can be used to estimate the contact time of an impact. A spherical impact contains a wide range of frequencies. The spherical impact with short contact times have a broader range of frequencies but low amplitude waves. The impacts with longer contact times have a narrower band of lower frequencies and higher amplitude waves. The low frequencies have longer wavelengths and travel longer and deeper in a medium. Short wavelengths have the advantage of detecting small defects but the disadvantage of having rapid attenuation and thus shallow penetration. The large diameter spheres are used to generate impacts with longer contact times and longer wavelengths, to detect deeper flaws or evaluate thicker structures. In order to evaluate the integrity of a medium, at least one full wavelength should travel the path length, back and forth, three full cycles. Thus, the choice of the impactor and its contact time depends on the thickness of the testing specimen and the size and the depth of the flaw or the reinforcement bars (in the case of concrete). The impact should generate waves having wavelengths smaller or equal to the thickness of the testing specimen. To detect a flaw within a media, the wavelengths should be smaller than its dimensions. Contact time of the impact should always be shorter than PP- or SS-wave arrivals.

To use the correct impact source for a specimen, first the required wavelengths should be determined. Later, the wavelengths should be converted to frequency by the equation $$V\lambda^{-1}$$

and knowing the elastic wave velocities in the specimen. In a solid, for a given impact the wavelengths of compressive waves are longer than shear waves. Therefore, the upper limit of wavelengths travelling the path length depends on the P-wave. Thus a contact time that is short enough to generate the required frequencies can be selected. An approximation for the upper limit on the usable frequency range generated by a given impact is given by $$\Delta f = \frac{1.25}{t_c}$$

Table 1 illustrates the relationship between the possible contact times that can be generated by spherical impact sources, and the range of frequencies, $\Delta f$, generated by the impact. The body wave velocities of steel, concrete, and granite were used to calculate the generated wavelengths for each contact time. It was assumed that the surface of the specimen are smooth and the impacts are repeatable.

For the vertical and horizontal displacement transducers, broadband piezoelectric transducers are more suitable for impact testings since the output signals are less tainted with the effects of transducer resonance (Carino, 1986). Also broadband transducers respond to signals over a wide frequency range.

TABLE 1

A Relationship Between Contact Time, Generated Frequencies, and Produced Wavelengths of Body Waves.

| Sphere Diameter (mm) | Contact Time ($t_c$) ($\mu s$) | Range of Frequencies ($\Delta f$) (kHz) | P-wavelength (m) (for a velocity of 6400.0 m/s) Steel | S-wavelength (m) (for a velocity of 4300.0 m/s) Steel | P-wavelength (m) (for a velocity of 4000.0 m/s) Concrete | S-wavelength (m) (for a velocity of 2300.0 m/s) Concrete | P-wavelength (m) (for a velocity of 4600.0 m/s) Granite | S-wavelength (m) (for a velocity of 2200.0 m/s) Granite |
|---|---|---|---|---|---|---|---|---|
| 1.4 | 10 | 0–125.0 | 0.05 | 0.03 | 0.03 | 0.02 | 0.04 | 0.02 |
| 2.9 | 15 | 0–83.3 | 0.08 | 0.05 | 0.05 | 0.03 | 0.06 | 0.03 |
| 4.8 | 25 | 0–50.0 | 0.13 | 0.09 | 0.08 | 0.05 | 0.09 | 0.04 |
| 6.4 | 35 | 0–35.7 | 0.18 | 0.12 | 0.11 | 0.07 | 0.13 | 0.06 |
| 7.9 | 45 | 0–27.7 | 0.23 | 0.16 | 0.14 | 0.08 | 0.17 | 0.08 |
| 9.5 | 55 | 0–22.7 | 0.28 | 0.19 | 0.18 | 0.10 | 0.20 | 0.10 |
| 11.1 | 65 | 0–19.2 | 0.33 | 0.22 | 0.21 | 0.12 | 0.24 | 0.11 |
| 12.7 | 75 | 0–16.7 | 0.38 | 0.26 | 0.24 | 0.14 | 0.28 | 0.13 |
| 13.4 | 85 | 0–14.7 | 0.44 | 0.29 | 0.27 | 0.16 | 0.31 | 0.15 |
| 14.9 | 95 | 0–13.2 | 0.48 | 0.33 | 0.30 | 0.17 | 0.39 | 0.17 |

TABLE 1
A Relationship Between Contact Time, Generated Frequencies, and Produced Wavelengths of Body Waves The vertical displacements are best detected by a sensitive piezoelectric vertical displacement transducer. The horizontal displacements are best detected by a sensitive piezoelectric horizontal displacement transducer. Both P- and S-waves are detected by the two types of transducers. For the vertical displacement transducers the vertical motion is generated by the P-wave as a result of both displacement and propagation vectors. The S-wave is detected as a result of the vertical displacements generated by the S-wave propagation vector. For the horizontal displacement transducer, the S-wave is detected due to the horizontal displacements caused by the S-wave displacement vector, P-wave is also detected by the horizontal displacement transducer, since every time a P-wave reaches the surface (at epicenter), it disperses along the surface. The P-wave propagation vector along the surface creates a horizontal displacement which is detected by the horizontal displacement transducer.

Figure 3:
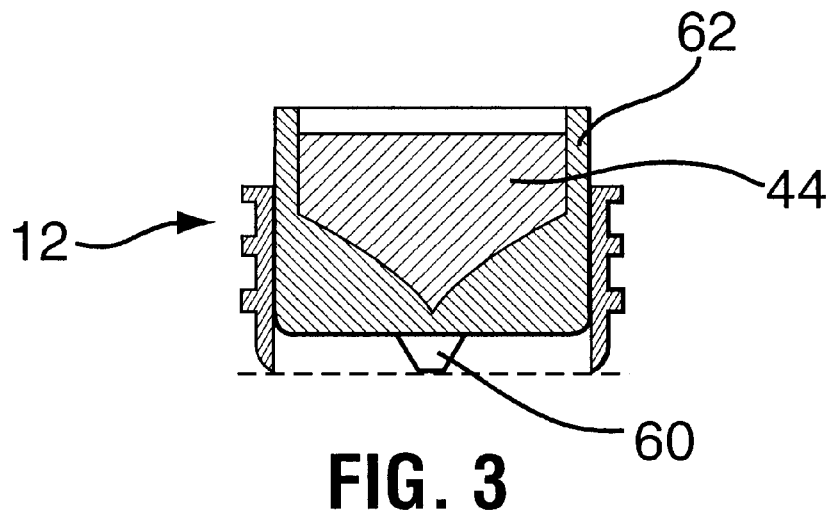
FIG. 3 is a cross-section through a vertical displacement transducer.

The vertical displacement transducer 13, is an IQI Model 501 dynamic piezoelectric transducers, developed by the National Bureau of Standards (NBS) (the name has changed to United States National Institute of Standards and Technology) illustrated in FIG. 3. This transducer (described in U.S. Pat. No. 4,782,701) has become known as NBS-conical transducer, has a response that is uniform over a wide frequency range, is directly related to displacement, and is sensitive almost exclusively to displacement normal to the surface. The NBS-conical transducer has a cone-shaped active element 60 made of lead-zirconite-titanate or commonly known as PZT. The aperture of the active element is 1.0 mm in diameter, smaller than any wavelengths of expected frequency ranges. The small contact area of the transducer makes it act as a point receiver. The Model 501 transducer offers the exceptional feature of very flat frequency response over the range 50 KHz to 1 MHz. Overall, the transducer is 21.0 mm in diameter and 18.4 mm thick. Two ends of the active element 60 are attached to silver electrodes. On one side the active element is fixed to a cylindrical brass backing 62 filled with tin and tungsten powder epoxy mix 44. The heavy brass backing causes dampening of undesirable frequencies. The transducer is mounted in a housing, and the brass backing is connected to a matching amplifier in the housing.

Figure 4:
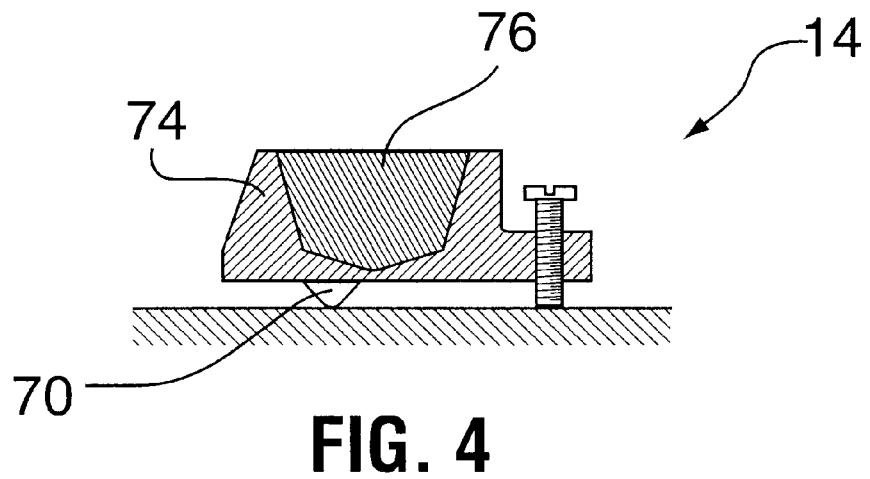
FIG. 4 is a cross-section through a horizontal displacement transducer.
Figure 5:
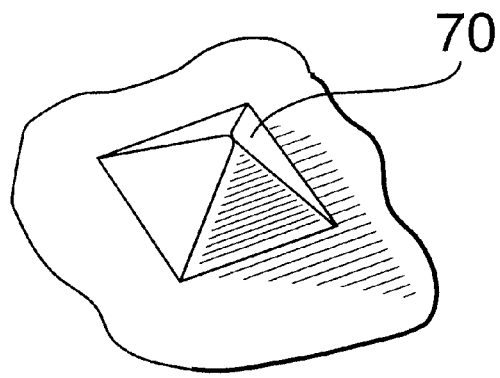
FIG. 5 is a perspective view of the active elements of the transducer illustrated in FIG. 4.

The horizontal displacement transducer 14 is of the form described in U.S. Pat. No. 4,782,701 and an example is illustrated in FIGS. 4 and 5. The horizontal displacement transducer 14 comprises the active element 70 of PZT and a component, matched backing in the form of a hollow brass shell 74 and a tin metal core 76. The active element 70 has the form of a truncated pyramid with a 12 mm square base and a 6 mm height. The aperture, which is the truncated end, is 0.5 mm by 2.0 mm with the smaller dimension in the direction of polarization (the direction of maximum tangential sensitivity). This is seen in FIG. 5. The brass shell 74 has the overall dimensions of 25.0 mm thick, 65.0 mm long, and 50.0 mm wide. A conical cavity is cut into the rear of the backing and filled with molten tin metal. The backing and the active element are attached by a low temperature tin-indium solder. The transducer's response is nearly flat and constant over 1.5 MHz (0 to 1.5 MHz) bandwidth. The transducer captures an output voltage waveform which is proportional to the tangential dynamic displacement. At the same time it has the minimal output when exposed to vertical displacement. The transducer displays directional behavior, having a null in signal output when the polarization direction is at right angle to the direction from the source. The transducer is mounted in a housing and the brass backing is connected to a matching amplifier also mounted in the housing. The output signal is transferred to a waveform analyzer by a BNC connector (maximum output voltage of ±2 volts, peak to peak).

The horizontal displacement transducer must be placed within a circle, with the impact source being the center of it and the radius being less than the S-wavelength. The distance between the impact source and the receiver ($d_r$) has to be determined based on the thickness of the plate and its estimated material properties. Once the angle of S-wave reflection is selected, the optimum horizontal displacements can be detected by the transducer. The piezoelectric tip of the transducer has a linear contact with the surface. The direction of the PZT linear tip of the transducer has to be at a right angle to the impact point.

Both transducers are cased in a way that can be functional in underground situations. The small tip of the transducers requires minimum surface preparation of the structures.

The MSR technique is designed in order to evaluate the materials by indirect method. That is, based on the miniature seismic reflection principles the data can be collected successfully from the same surface the signal was generated into the medium. For the evaluation of the elastic properties of concrete and rocks, the direct method can also be used. In the direct method the impact source and the receiver are on two opposite sides of a sample.

For optimum signals, the tangential transducer is spaced from the impact device by a distance equal to the thickness being measured, although circumstances may make such optimum positioning impossible.

The signals are processed in the computer in a normal manner, and in accordance with well known programs.

A Comparison Between the MSR System and Other Wave Propagation Techniques

One advantage of the MSR technique over traditional non-destructive methods such as resonance frequency, ultrasonic pulse velocity (UPV), and impulse-response techniques is that accurate readings may be obtained from a free surface regardless of the dimensions and condition of the concrete structure. The main advantage of the MSR system over the impact-echo technique is the presence of additional tangential displacement transducer in the system and also the multi-strength/multi-diametrical impact devices. These additional enhancement features provides the MSR system with the capability of measuring direct shear wave parameters and as a result the data can be used to calculate the dynamic elastic constants of the testing structure at every point on the structure. The MSR system in comparison with the pulse-echo techniques uses a more accurate and easy to operate interpretation technique (frequency domain verses time domain). In comparison with the SASW technique, MSR system has the capability of measuring dynamic elastic properties without assuming various models and ratios. The MSR system in comparison with the petite sismique and seismic wave velocity techniques operates in a smaller and more detailed scale. Table 2 below illustrates the above-referred to advantages and disadvantages.

TABLE 2

A Comparison Between MSR System and the NDT & E
Techniques Capable of Measuring Dynamic Elastic Moduli
Dynamic Modulus of Elasticity Measuring Techniques

| Technique | Concrete | | Rock | | Advantages | Disadvantages |
| --- | --- | --- | --- | --- | --- | --- |
| | Lab. | Field | Lab. | Field | | |
| Resonance Frequency | X | X | X | — | Calculates the natural frequency of different vibration modes. Calculates the elastic moduli. Relatively inexpensive. Extensively used. | The dimensions of the specimen control the testing procedure. It is not comonly used in the field. Needs to have access to the specimen from various directions |
| Ultrasonic Pulse Velocity | X | X | X | X | Direct P-wave velocity measurement. Easy to use. Fast measurement technique. Time saving. Inexpensive. Extensively used. | Difficult to measure S-wave parameters. Usually assumes Poisson's ratio or shear wave velocity for elastic moduli measurement. Rapid signal attenuation problem. Best functions if it has two side access to the specimen. |
| Seismic Wave Velocity | — | X | — | X | Direct elastic wave measurement. Used for large scale measurements. Could be inexpensive (i.e. hammer seismmic). Extensively used. | Difficult to recognize S-wave parameters. Could be expensive (i.e. borehole, and use of explosives). Best functions if it has two side access to the specimen. |
| Petite Sismique | — | — | — | X | Direct measurement of S-wave parameters. Comparison of static modulus of elasticity with S-wave parameters. It functions from one accessible side to the specimen. | Difficulty in generation and detection of S-waves. Presently in experimental stages. Can be expensive (i.e. source and receiver). |
| Impulse-Response | — | X | — | — | Measures the elastic moduli of the concrete piles and it's basement material. It functions from one accessible side to the specimen. Inexpensive. | Indirect calculations of modulus values. It is limited to the piles or columnar structures. |
| SASW | — | X | — | — | Capable of measuring modulus of eleasticity for thin pavement layers. It functions from one accessible side to the specimen. Inexpensive. | Calculates the elastic moduli values by comparing with various models. Assumes theoretical Poisson's ratio values for calculations. Rapid R-wave attenuation in thick concrete layers. |
| Impact-Echo | X | X | — | — | Direct measurements of P-wave parameters Capable of detecting and locating flaws. It functions from one accessible side to the specimen. Inexpensive. Time saving. | Very thin layers (i.e. below 10 cm. are difficult to detect. |
| MSR | X | X | X | X | Direct measurements of P- and S-wave parameters. Capable of detecting and locating flaws. It functions from one accessible side to the specimen. Capable of measuring the elastic constants. Time saving. Inexpensive. | Very thin layers (i.e. below 10 cm. are difficult to detect. frow one accessible side io |

The apparatus, and method, as described, is useful for manual use inside fairly large diameter bores, such as concrete pipes, concrete lined bores, and similar structures, being small enough to be carried by operators into such structures. It is possible to reduce the size of the impact device, and transducers, such that they can be mounted on a carrier member for passage through smaller bores, with positioning and actuation of the impact device and transducers, by remote control.

While primarily considered for use in artificial material structures, such as concrete lined bores, concrete pipes and other structures, the invention can also be used with respect to natural materials. For example, the invention can be applied in bores in rock and with respect to other rock structures. Faults in the rock and deterioration in joints between rock members, can be detected.

The apparatus provides information of varying forms depending upon the actual situation. The signals impacted to the structure by the impact devices are reflected by an interface. Such an interface can be of many forms. Thus in a concrete pipe, the interface can be between the pipe and the surrounding structure. Deterioration of the outside surface of the pipe can be detected. The interface can be formed by a crack in the structure, such as a concrete pipe, or wall, or in an rock structure. An interface can occur at a void in a structure. It can be formed by an inclusion, such as reinforcement. Any change in the homogeneous structure can result in an interface and can be detected, and its position measured.

It can also be arranged that the impact device produces a signal indicative of actuation. This signal can be produced by making of contacts in the impact device. This signal can be input to the computer by a connection 80 (FIG. 1).

We claim:

1. A method for the non-destructive evaluation of deterioration of subsurface material structures occurring at an interface between the structure and the surrounding soil or rock, comprising:

impacting a spherical surface on a surface of a structure;

detecting reflected signals from said interface in said structure by a vertical displacement transducer;

detecting reflected signals from said interface in said structure by a horizontal displacement transducer; and processing signals from said transducers to produce a measurement between said surface and said interface and a measurement of the physical properties of the structures.

2. The method as claimed in claim 1, including holding said impact device and said transducers against said surface of said structures.

3. The method as claimed in claim 1, including converting analogue signals from said transducers to digital signals.

4. The method as claimed in claim 3, including converting said signals from time domain to frequency domain.

5. The method as claimed in claim 1, including producing a signal indicative of impacting said spherical surface against said surface of said structure.

6. The method as claimed in claim 1, including impacting a ball forming said spherical surface against said surface of said structure.

* * * * *